United States Patent [19]

Forschner

[11] Patent Number: 5,310,945
[45] Date of Patent: May 10, 1994

[54] PROCESS FOR PREPARING PARA-DIOXANONES

[75] Inventor: Thomas C. Forschner, Richmond, Tex.

[73] Assignee: Shell Oil Company, Houston, Tex.

[21] Appl. No.: 996,218

[22] Filed: Dec. 23, 1992

[51] Int. Cl.⁵ .......................... C07D 319/12
[52] U.S. Cl. ................................. 549/274
[58] Field of Search .................. 549/378, 274

[56] References Cited

U.S. PATENT DOCUMENTS

| | | |
|---|---|---|
| 2,807,629 | 9/1957 | Bell . |
| 2,900,395 | 8/1959 | Guest et al. . |
| 3,119,840 | 1/1964 | Mayhew et al. . |
| 4,600,529 | 7/1986 | Hallen et al. . |
| 4,789,502 | 12/1988 | Slaugh . |
| 5,110,954 | 5/1992 | Bellis . |

FOREIGN PATENT DOCUMENTS 1593697A 12/1988 U.S.S.R. .

Primary Examiner—Nicky Chan

[57] ABSTRACT

A highly selective dehydrogenation catalyst for the preparation of para-dioxanones is produced by impregnating copper and zinc on a promoter impregnated support. This catalyst is effective for the dehydrogenation of dialkylene glycols to produce a high purity 2-para-dioxanones.

23 Claims, No Drawings

PROCESS FOR PREPARING PARA-DIOXANONES

FIELD OF INVENTION

This invention relates to preparation of paradioxanones. In a specific aspect, the invention relates to a process to produce para-dioxanones by oxidative dehydrogenation of dialkylene glycols.

BACKGROUND OF THE INVENTION

Para-dioxanones are used as a starting material in the manufacture of poly para-dioxanones. The poly para-dioxanones are used in the manufacture of adsorbable monofilament suture fibers and other adsorbable medical devices.

One method of preparing para-dioxanones is by oxidative dehydrogenation of dialkylene glycols. In U.S. Pat. Nos. 2,900,395 and 2,807,629, a copper chromite catalyst is used for the oxidation dehydrogenation of diethylene glycol. However, these patents report a yield of about 67–84% and a conversion of about 67–94%.

It has been found that the presence of impurities inhibit polymerization. Typical impurities in the preparation of 2-para-dioxanone include, unreacted dialkylene glycol and reaction by-products such as 2-para-dioxanol, para-dioxane, 2,3dihydro-para-dioxin (dioxene), alkylene glycol and carboxylic acids. Particularly, the production of carboxylic acids and hydroxylic compounds can hinder polymerization of 2-paradioxanones. Therefore, a process to produce a high purity paradioxanone ("polymerization grade") is desirable.

It is therefore an object of the present invention to provide a para-dioxanone preparation process with high conversion rate and selectivity.

SUMMARY OF THE INVENTION

According to the invention, a process for the production of para-dioxanones is provided, by contacting a dialkylene glycol at a temperature within the range of about 200° C. to about 400° C. with an effective amount of a dehydrogenation catalyst comprising catalytically effective amounts of copper, zinc and a promoter selected from the group consisting of alkali metals and alkaline earth metals and mixtures thereof supported on alumina.

DETAILED DESCRIPTION OF THE INVENTION

It has been found that 2-para-dioxanones can be produced in high yields with minimal side-reactions by contacting a dialkylene glycol with an effective amount of a dehydrogenation catalyst comprising catalytically effective amounts of copper, zinc, a promoter and optionally chromium supported on an alumina. Further, it has been found that by preferably impregnating the alumina with a promoter prior to metal mixture impregnation, a dehydrogenation catalyst which has conversion as high as about 100% and/or selectivity as high as about 98% can be obtained.

Dehydrogenation Catalyst

Suitable promoters can be compounds (including, salts, compounds and complexes) of alkali metals and alkaline earth metals. The promoters must be soluble in a suitable solubilizing media, either organic or inorganic. Water is a preferred solubilizing media. Lower alkanols and ethers also provide examples of suitable organic solvents. Preferred promoters include, for example, compounds of sodium, potassium, lithium, calcium, magnesium and mixtures thereof. The promoter is typically present in an amount sufficient to suppress paradioxane formation. The promoter is preferably present in an amount of from about 0.1 to about 20 weight percent, more preferably from about 0.5 to about 10 weight percent measured as the metal per total weight of the dehydrogenation catalyst. The optimum catalyst contains about 1 to about 5 weight percent of promoter measured as the metal per total weight of the catalyst.

The carrier utilized in the catalyst of the invention is an alumina. A porous alumina, more preferably a gamma-alumina, having a B. E. T. surface area greater than about 100 $m^2/g$ is preferred. An alumina with a lower surface area than 100 $m^2/g$ is also acceptable, however, activity decreases with decreasing surface area while maintaining the selectivity level of the dehydrogenation catalyst. The B. E. T. method for determining specific surface area is described in detail in Brunauer, S., Emmet, P. H., and Teller, E. J., *J. Am. Chem. Soc.*, 60, 309–16 (1938). The most suitable aluminas for use in the present invention are found to be those having a high surface area, for instance, alumina having a surface area of at least about 100 $m^2/g$. The alumina may contain minor amounts of other compounds such as silica (i.e., less than 50 weight percent). Large amounts of silica increases the presence of impurities in the reaction product and should be avoided. Suitable commercial aluminas include, Vista Catapal Series; AX-200 type from Criterion Catalyst Co., L. P.; and A-201 from La Roche Aluminas.

The dehydrogenation catalyst can be prepared by impregnating the alumina support with solubilized compounds (including, salts, compounds and complexes) of copper, zinc, a promoter, and optionally chromium. The impregnation can be carried out in any order or simultaneously. In a preferred embodiment, the promoter is first impregnated on the alumina support, then dried and optionally calcined. The dried (or calcined) material is then impregnated with a solution having copper, zinc and optionally chromium compounds dissolved therein. The solution of copper, zinc and chromium compounds can be impregnated in one step by using a single solution with copper, zinc and optionally chromium compounds dissolved or impregnated in a multi-step process, using one or more of copper, zinc and optionally chromium compounds dissolved in individual impregnating solutions. It is preferred to use just a sufficient amount of impregnating solution containing all the requisite metal compounds such that all the pore volume in the support is filled and no excess solution is left after impregnation.

The alkali and alkaline earth promoters can be impregnated on alumina in the form of compounds (including, salts, compounds and complexes) such as, for example, hydroxides, chlorides, bromides, nitrates, acetates, lactates, carbonates, bicarbonates, oxides, oxalates, sulfates and the like. Carbonates and bicarbonates are preferred because of ease of use. Suitable copper, zinc and chromium compounds includes, for example, chlorides, bromides, nitrates, acetates, lactates, carbonates, bicarbonates, oxides, oxalates, sulfates and the like. Nitrates are preferred for ease of decomposition.

This material after impregnation with catalytic components is dried and calcined. The drying step is typically carried out at temperatures up to about 150° C., preferably at a temperature within the range of from about 80° C. to about 150° C. The calcination step is typically carried out at a temperature within the range of from about 100° C. to about 900° C., preferably from about 300° C. to about 800° C. The drying and calcining steps can be carried out in one continuous step, heating the material slowly through the low temperature ranges to dry the material and then raising the temperature to the calcining conditions. The drying step is preferably carried out in the initial stages of the calcination step if calcining immediately after drying. The impregnated material is calcined to convert the soluble metal compounds to oxides or oxygen-containing compounds upon the alumina support. Calcining is carried out in a neutral or oxidizing atmosphere, air being the preferred atmosphere. Nitrogen is also a suitable alternative atmosphere. The times for the drying and calcining steps are not critical and are dependent upon the temperatures utilized. The drying and calcining times are typically in the range of from about five minutes to about twenty four hours, although longer times are acceptable.

The calcined material is then activated by subjecting the catalyst to a reducing condition prior to use. The reducing condition may be either a gaseous atmosphere or a suitable liquid solution.

Suitable examples of a gaseous reducing atmosphere comprise hydrogen, ammonia, carbon monoxide, mixtures thereof and the like. The gaseous reducing atmosphere may also optionally contain inert gases such as nitrogen. The preferred atmosphere is hydrogen. Activation temperatures when utilizing a gaseous atmosphere range from about 175° C. to about 550° C. The time needed for activation in a gaseous atmosphere will depend on the temperature, the higher the temperature, the shorter the time and the lower the temperature, the longer the activation. Typically, useful times have been found to range from about 0.01 hour to about 24 hours. Although times outside these limits are also useful, economic considerations generally dictate that longer times not be used. It is preferable, after conversion of the metal compounds to the oxides, to slowly ramp the temperature (eg. 0.1° to 2° C. per minute) up to the activation temperature in the presence of reducing atmosphere. This procedure increase the lifetime of the catalyst.

Liquid solutions suitable for providing reducing conditions include, for example, aqueous or ammoniacal solutions of hydrozine, sodium borohydride or formaldehyde or solutions of triethyl aluminum or di-isobutyl aluminum hydride in an organic solvent such as heptane. The catalysts can be activated using reducing liquid solutions within a range of from about 25° C. or higher, preferably from about 25° C. to about 100° C., for a time of from about 0.01 hours to about 10 hours or longer. Temperatures and time are not critical and are dependent upon the reducing solution being utilized.

While not wishing to be bound by any particular theory, it is believed that the activation of the catalyst under reducing conditions at least partially reduces the copper from the +2 valence state to the +1 and/or 0 valance state, which is believed to contribute to the catalytic activity of the catalyst. Reducing conditions, however, preferably should not be so severe as to reduce the zinc oxides and chromium oxides. The promoters preferably, even after subjecting to reducing conditions, will not be present on the catalyst in the form of the active free metal but will be present in oxidized form. They are believed to be present in the form of oxides or oxygencontaining compounds and may be combined with the alumina support and/or other catalyst components.

The appropriate activation conditions can readily be determined by experimentation. For example, times and temperatures can be varied and the resultant catalytic material can be examined by x-ray photoelectron spectroscopy in order to determine the activation state of the copper. Alternatively, the catalyst's catalytic activity can be determined and utilized to determine optimum activating conditions.

The amount of metals deposited upon the support are not critical and may be varied through a wide range so long as they are present in sufficient amount to be catalytically effective. Preferably copper is present in an amount of about 1 to about 35 weight percent, more preferably about 1 to about 15 weight percent measured as metal per total weight of the dehydrogenation catalyst. Preferably zinc is present in a mole ratio of zinc to copper of from about 0.01:1 to about 5:1, more preferably from about 0 01:1 to about 1.5:1. Chromium can optionally be present in an amount of about 0 to about 25 weight percent measured as metal per total weight of the dehydrogenation catalyst.

Preparation of Para-dioxanones

The dialkylene glycol corresponding to the desired optionally alkyl-substituted 2-para-dioxanone is contacted, in a reaction zone, with an effective amount of a dehydrogenation catalyst (prepared as described above) to produce the paradioxanone at a temperature within the range of from about 200° C. to about 400° C., preferably from about 250° C. to about 300° C. A temperature of less than about 300° C. is preferred for longer catalyst life. The reaction is carried out at a pressure within the range of about 0.1 atmosphere to about 20 atmosphere, preferably from about 0.5 atmosphere to about 5 atmosphere.

In a particularly preferred embodiment, the dehydrogenation catalyst preferably does not contain chromium for environmental disposal reasons. For longer catalyst lifetime, dehydrogenation catalysts having a relatively higher copper loading, for instance, alumina having copper in the amount of at least 4 weight percent measured as metal per total weight of the dehydrogenation catalyst is preferred. Promoter is preferably present in an amount of less than about 15 weight percent measured as metal per total weight of the dehydrogenation catalyst to minimize side-reactions.

The inventive process can be carried out in vapor phase, liquid phase or can be refluxed in the presence of the dehydrogenation catalyst. The reaction is preferably carried out neat, but can be in an inert solvent or environment. The process can further be carried out in a batch process or in a continuous process.

In a continuous process, the liquid hourly space velocity (LHSV) at the reaction zone is at a rate effective to form para-dioxanones, preferably within the range of from about 0.1 to about 8 $h^{-1}$, more preferably from about 0.1 to about 3 $h^{-1}$. The reaction is preferably carried out in an neutral to reducing environment such as, for example, nitrogen or argon atmosphere (inert gas) optionally containing hydrogen. Pure hydrogen atmosphere can also be suitable. Currently, the reaction is more preferably carried out in an inert gas/hydrogen atmosphere containing hydrogen to inert gas ratio from about 1:0.01 to 1:50. In a particularly preferred embodiment, the process is carried out continuously at a temperature in the range of from about 260° C. to about 290° C., a pressure in the range of from about 0.5 atmosphere to about 2 atmosphere and a LHSV within the range of from about 0.5 to about 2 h$^{-1}$. The process can be carried out in fluidized beds or packed columns, with packed columns being preferred due to ease of operation.

In a batch process, the catalyst is present in an amount effective to form para-dioxanones, preferably in an amount of from about 0.1 weight percent to about 50 weight percent, more preferably from about 1 weight percent to about 20 weight percent based on the weight of the dialkylene glycol.

Suitable dialkylene glycol can be represented by the formula

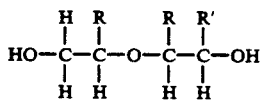

in which each R and R' are independently hydrogen or $C_{1-20}$ alkyl. Preferably R' is hydrogen. Preferably R is independently hydrogen or $C_{1-12}$, most preferably hydrogen or $C_{1-2}$. Examples of the most preferable dialkylene glycols include, diethylene glycol, dipropylene glycol and dibutylene glycol. The inventive process is especially suitable for production of 2-para-dioxanone by the dehydrogenation of diethylene glycol.

The dehydrogenation catalyst can be regenerated after use or during use to extend the catalyst life and/or to obtain higher overall conversion and selectivity. The regeneration can be performed at any convenient time as necessary. For example, the spent catalyst can be regenerated in situ or removed from the reactor and regenerated separately.

The catalyst can be regenerated by heating the catalyst at a temperature within the range of about 100° C. to about 900° C., preferably from about 300° C. to about 800° C. in a neutral or oxidizing atmosphere, air being the preferred atmosphere. Nitrogen or oxygen or a mixture thereof are also suitable atmosphere. For example, in a continuous process, the catalyst can be regenerated in situ by first stopping the flow of the feed over the catalyst and cooling the catalyst to about room temperature. Then the catalyst can be regenerated by contacting the catalyst in a neutral or oxidizing atmosphere at an elevated temperature with a flow of the atmosphere. After the catalyst is regenerated, the catalyst is reactivated prior to use.

The inventive process allows formation of highly pure 2-para-dioxanone with minimal side-reactions. Impurities such as carboxylic acids, hydroxylic compounds and dioxane are minimized while obtaining high conversion and selectivity.

Illustrative Embodiment

The following illustrative embodiments describe the process of the invention and are provided for illustrative purposes and are not meant as limiting the invention.

EXAMPLE 1

This example demonstrates preparation of a dehydrogenation catalyst according to the inventive process.

A solution of 2.04 g (13.3 mmol) $K_2CO_3$ in 30 mL of distilled water was added slowly to 50.20 g of neutral γ-Alumina with a surface area of 120 m²/g (AX-200 from Criterion Catalyst Co., L. P.). The impregnated catalyst was then dried at 100° C. After drying, 6.82g (36.0 mmol) $Zn(NO_3)_2 \cdot 6H_2O$ and 18.73 g (80.5 mmol) $Cu(NO_3)_2 \cdot 2.5H_2O$ dissolved into 40 mL of distilled water was added slowly to the catalyst. The catalyst was stirred as the solution was added to evenly distribute the solution over the material. The solid was then dried overnight at 120° C. under $N_2$.

COMPARATIVE EXAMPLE A

A copper/zinc/chromium catalyst was made as a comparative catalyst.

Copper Nitrate (36.42 g), chromium nitrate (10.11 g), and zinc nitrate (6.82 g) were added to 100 mL of deionized water. The resulting solution was heated to 90° C. and added to a stirred aqueous (600 mL) solution of potassium carbonate (30.63 g), also at 90° C. The resulting mixture was allowed to cool to room temperature with stirring, before the solids were filtered off. The cake was washed with 4 liter of deionized water and vacuum dried for 2 days. The solid cake was then sieved to 40-20 mesh for use in the flow reactor.

COMPARATIVE EXAMPLE B

A copper/zinc on alumina catalyst was made as a comparative catalyst.

A 20 mL solution containing zinc nitrate (4.85 g) and copper nitrate (10.72 g) was slowly added to 36.12 g of neutral γ-Alumina with a surface area of 120 m²/g (AX-200 from Criterion Catalyst Co., L. P.). The resulting catalyst was then dried at 150° C. under vacuum for 24 hours.

COMPARATIVE EXAMPLE C

A copper/zinc/potassium on carbon catalyst was made as a comparative catalyst.

A solution of 2.09 g potassium carbonate and 20 mL of distilled water was slowly added to 35 g of dried CAL (Activated Carbon from Calgon). The catalyst was then dried at 80° C. under vacuum. After cooling to room temperature, an aqueous solution (30mL) containing zinc nitrate (5.8 g) and copper nitrate (15.0 g) was added slowly with stirring. The catalyst was then dried at 80° C. under vacuum.

EXAMPLE 2

This example demonstrates preparation of another dehydrogenation catalyst useful in the inventive process.

A 15.3 g portion of the above catalyst from Comparative Example B was treated with an aqueous (10mL) potassium carbonate (0.65 g) solution The catalyst was then dried at 150° C. under vacuum.

EXAMPLE 3

This example demonstrates preparation of another dehydrogenation catalyst useful in the inventive process.

A solution of 4.01 g of potassium carbonate was dissolved in 60 mL of water and slowly added to 50.35 g of neutral γ-Alumina with a surface area of 120 m²/g (AX-200 from Criterion Catalyst Co., L. P.). The excess water was then removed by heating at 100° C. After drying, a 40 mL aqueous solution containing 6.77 g of zinc nitrate and 14.98 g of copper nitrate was slowly added to the catalyst. The catalyst was then dried overnight at 100° C. under vacuum.

EXAMPLE 4

This example demonstrates preparation of another dehydrogenation catalyst useful in the inventive process.

A 30 mL aqueous solution containing 4.08 g of potassium carbonate was slowly added to 50.2 g of neutral γ-Alumina with a surface area of 120 m²/g (AX-200 from Criterion Catalyst Co., L. P.). The mixture was allowed to sit for 30 minutes to allow the solution to penetrate all of the catalyst. The excess water was then removed by heating at 100° C. The catalyst was then impregnated with 6.82 g zinc nitrate and 18.73 g of copper nitrate dissolved in 40 mL of water. The sample was then dried overnight at 120° C. under vacuum.

Catalyst Activation

Each of the above catalyst were activated in a similar manner. The catalyst was loaded into a stainless steel flow reactor atop of a 10–15 cm bed of silicon carbide. The temperature was slowly raised to 375° C. while the reactor is purged with air. After all of the nitrate salts have decomposed (2 hours), the reactor is cooled to 150° C. At 150° C., the air flow is stopped and a 1:5 hydrogen/nitrogen gas is introduced into the reactor. The temperature is then slowly increased to 275° C. at a rate of 0.5° C. per minute.

Examples 5–8 and Comparative Examples D–F

This example demonstrates preparation of 2-paradioxanone from diethylene glycol according to the inventive process using catalysts from Examples 1, 2, 3 and 4 respectively Examples 5, 6, 7 and 8. Further, para-dioxanone was prepared using catalysts from Comparative Examples A, B and C, respectively Comparative Examples D, E and F.

For all of the Examples, the following procedure was used using the catalyst amounts and reactor conditions listed in Table 1. A stainless steel flow reactor was fitted with a sample receiver connected to the vent with a gas flow meter in line.

Nitrogen gas flow as adjusted to 250 mL min⁻¹ and the temperature raised to 120° C. for 1 hour. After all the water has come off, the temperature was raised stepwise to 150° C. and 50° C. every 30 minutes thereafter or slowly ramped until reaching the final temperature listed in Table 1.

The reactor was cooled down to room temperature, and the hydrogen flow adjusted to 50 mL min⁻¹ for a total hydrogen and nitrogen gas flow of listed in Table 1. The catalyst bed was then slowly heated at 0.5° C. per minute to 275° C.

The feed pump was started at 0.20 mL min⁻¹ and samples were collected every hour (1-4 hours) to confirm acceptable conversion and selectivity by GC-MS analysis.

For Example 5, catalyst was regenerated by first stopping the flow of feed over the catalyst and cooling to room temperature. The nitrogen/hydrogen sweep was stopped and air was flowed over the catalyst as the temperature is raised to 450° C. at a rate of 0.1 to 1° C. per minute. The catalyst is then cooled to room temperature, the sweeping gas is switched to nitrogen/hydrogen gas and the temperature is raised to 275° C. at a rate of 0.1° to 1° C. per minute. The catalyst was regenerated when the conversion dropped below 88%. The reactor ran continuously for 140 hours at 100% conversion and 96-99% selectivity to 2-para-dioxanone. Major side product identified was 1,4-dioxane.

For Examples 6–8 and Comparative Examples D–F, 2-dioxanone was prepared in a similar manner to Example 5, except, catalyst from Examples 2–4 and Comparative Examples A–C were used, respectively. All of the other Examples were run between 200 to 800 hours without regenerating the catalyst. The conditions of reaction (amount of catalyst, LHSV, total hydrogen and nitrogen gas flow, and temperature) are listed in Table 1 below.

Percent conversion and selectivity are listed in Table 1 below.

TABLE 1

| | Catalyst Amount (ml) | Conditions | | | Results | | | | |
|---|---|---|---|---|---|---|---|---|---|
| | | LHSV | Flow ml/min | Temp °C. | % Conversion | % PDX[a] | % Selectivity % Dioxane | % HOAC[b] | Comment |
| Example 5 | 35 | 0.5 | 300 | 350 | 100 | 96-99 | >1 | >1 | |
| Example 6 | 20 | 0.90 | 200 | 250 | 82.0 | 73.7 | 2.6 | 3.8 | A |
| | " | 0.30 | " | " | 81.9 | 76.4 | 3.3 | | B |
| | " | 0.90 | " | 300 | 93.1 | 87.0 | 2.8 | 1.8 | |
| Example 7 | 40 | 0.60 | 300 | 279 | 99.6 | 95.8 | 2.4 | 0.3 | |
| Example 8 | 35 | 0.34 | 300 | 280 | 100.0 | 97.7 | 1.0 | 0.4 | |
| Comp. Ex D | 15 | 0.40 | 380 | 300 | 14.3 | 5.5 | | | |
| | " | " | " | 350 | 48.1 | 20.5 | 4.5 | 3.2 | |
| Comp. Ex E | 20 | 0.30 | 250 | 250 | 100.0 | 11.3 | 47.5 | 6.6 | C |
| | " | 0.90 | " | " | 100.0 | 56.5 | 25.9 | 4.7 | D |
| | " | 1.20 | " | " | 95.0 | 52.7 | 27.0 | | E |
| Comp. Ex F | 35 | 0.69 | 300 | 250 | 89.7 | 19.0 | 1.2 | 16.0 | |

A—Dioxanol 2.5%
B—Dioxanol 2.1%
C—Dioxene 3.9%
D—Dioxene 6.9%
E—Dioxene 14.7%
[a]—2-para-dioxanone
[b]—Acetic acid charged with catalyst from the respective Examples between silicon carbide and glass wool layers (at the ends). The reactor was installed on a Lindberg furnace and connected to a nitrogen, hydrogen and feed lines on the top of the reactor. An outlet from the reactor was

I claim:
1. In a process for the production of para-dioxanones by the catalytic dehydrogenation of dialkylene glycols, the improvement which comprises:
  contacting a dialkylene glycol at a temperature within the range of about 200° C. to about 400° C.

with an effective amount of a dehydrogenation catalyst comprising catalytically effective amounts of copper, zinc and a promoter selected from the group consisting of alkali metals and alkaline earth metals and mixtures thereof supported on an alumina.

2. The process of claim 1 wherein the dialkylene glycol is contacted with the catalyst at a temperature of less than about 300° C.

3. The process of claim 2 wherein the promoter is selected from the group consisting of sodium, potassium, lithium, calcium, magnesium and mixtures thereof.

4. The process of claim 3 wherein the promoter is potassium.

5. The process of claim 3 wherein zinc is present in a mole ratio of zinc to copper of about 0.01:1 to about 1.5:1.

6. The process of claim 5 wherein copper is present as measured as the metal in an amount of about 1 weight percent to about 35 weight percent based on the dehydrogenation catalyst.

7. The process of claim 6 wherein the promoter is present as measured as the metal is an amount of about 0.1 to about 20 weight percent based on dehydrogenation catalyst.

8. The process of claim 7 wherein the dehydrogenation catalyst further comprises chromium.

9. In a process for the production of para-dioxanones by the catalytic dehydrogenation of dialkylene glycols, the improvement which comprises:

contacting a dialkylene glycol at a temperature within the range of about 200° C. to about 400° C. with an effective amount of a dehydrogenation catalyst produced by (a) impregnating an alumina with a promoter selected from the group consisting of alkali metal compounds and alkaline earth metal compounds, (b) subjecting the thus-impregnated alumina to a temperature within the range of about 80° C. to about 900° C., (c) impregnating at least one zinc compound and at least one copper compound on the alumina from step (b) to form a dehydrogenation catalyst, (d) calcining the dehydrogenation catalyst at a temperature within the range of about 100° C. to about 900° C., and (e) reducing the calcined dehydrogenation catalyst to activate the dehydrogenation catalyst.

10. The process of claim 9 wherein the promoter is selected from the group consisting of sodium, potassium, lithium, calcium, magnesium compounds and mixtures thereof.

11. The process of claim 9 wherein the promoter is selected from the group consisting of alkali metal and alkaline earth metal hydroxides, chlorides, bromides, nitrates, acetates, lactates, carbonates, bicarbonates, oxides, oxalates and sulfates.

12. The process of claim 11 wherein the promoter is present as measured as the metal in an amount of about 0.1 to about 20 weight percent based on the dehydrogenation catalyst.

13. The process of claim 12 wherein the promoter is potassium carbonate or potassium bicarbonate.

14. The process of claim 12 wherein copper compound is present as measured as the metal in an amount of about 0.1 to about 35 weight percent based on dehydrogenation catalyst.

15. The process of claim 14 wherein the zinc compound is present in a mole ratio of zinc to copper of about 0.01:1 to 1.5:1.

16. The process of claim 15 wherein the copper compound is selected from the group consisting of copper nitrate, copper acetate, copper oxide, copper oxalate, copper sulfate and copper chloride.

17. The process of claim 16 wherein the zinc compound is selected from the group consisting of zinc nitrate, zinc acetate, zinc oxide, zinc oxalate, zinc sulfate and zinc chloride.

18. The process of claim 9 wherein, in step (c), further impregnating at least one chromium compound on the alumina.

19. The process of claim 18 wherein the promoter is potassium carbonate.

20. The process of claim 9 wherein the dialkylene glycol is contacted with the dehydrogenation catalyst at a liquid hourly space velocity within the range of from about $0.1\ h^{-1}$ to about $8\ h^{-1}$.

21. In a process for the production of para-dioxanones by the catalytic dehydrogenation of diethylene glycol, the improvement which comprises:

contacting diethylene glycol with a dehydrogenation catalyst at a temperature within the range of about 250° C. to about 300° C. and at a liquid hourly space velocity within the range from about $0.1\ h^{-1}$ to about $3\ h^{-1}$, said dehydrogenation catalyst is produced by (a) impregnating a $\gamma$-alumina with a potassium compound, (b) subjecting the thus-impregnated alumina to a temperature within the range of about 80° C. to about 900° C., (c) impregnating at least one zinc compound and at least one copper compound on the alumina from step (b) to form a dehydrogenation catalyst, (d) calcining the dehydrogenation catalyst at a temperature within the range of about 100° C. to about 900° C., and (e) contacting the calcined dehydrogenation catalyst with a reducing atmosphere comprising a gas selected from the group consisting of hydrogen, ammonia, carbon dioxide and mixture thereof at a temperature within the range of about 175° C. to about 550° C.

22. The process of claim 21 wherein the promoter is potassium carbonate.

23. The process of claim 22 wherein the copper compound is copper nitrate and the zinc compound is zinc nitrate.

* * * * *